US00PP35016P2

(12) United States Plant Patent
Fazio et al.

(10) Patent No.: US PP35,016 P2
(45) Date of Patent: Mar. 7, 2023

(54) APPLE TREE ROOTSTOCK NAMED 'G.257'

(50) Latin Name: ***Malus domestica* x *Malus robusta* hybrid**
Varietal Denomination: G.257

(71) Applicants: Cornell University, Ithaca, NY (US); The United States of America, as Represented by the Secretary of Agriculture, Washington, DC (US)

(72) Inventors: Gennaro Fazio, Geneva, NY (US); Terence Lee Robinson, Geneva, NY (US); Herbert Sanders Aldwinckle, Geneva, NY (US); James N. Cummins, Alcoa, TN (US)

(73) Assignees: Cornell University, Ithaca, NY (US); The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/589,353

(22) Filed: Jan. 31, 2022

(51) Int. Cl.
*A01H 5/08* (2018.01)
*A01H 6/74* (2018.01)

(52) U.S. Cl.
USPC ..... Plt./174

(58) Field of Classification Search
USPC ..... Plt./161, 174
See application file for complete search history.

(56) References Cited

U.S. PATENT DOCUMENTS

| | | | | |
|---|---|---|---|---|
| PP7,197 | P | 3/1990 | Luby et al. | |
| PP22,228 | P3 | 11/2011 | Brown et al. | |
| PP23,337 | P3 * | 1/2013 | Cummins | A01H 5/08 Plt./174 |
| PP24,073 | P3 * | 12/2013 | Cummins | A01H 6/7418 Plt./174 |

OTHER PUBLICATIONS

Mazzola, (1998). "Elucidation of the microbial complex having a causal role in the development of apple replant disease in Washington," Phytopathology, 88(9):930-938.
Unpublished U.S. Appl. No. 17/589,324, filed Jan. 31, 2022 titled "Apple Tree Rootstock Named 'G.484',".
Unpublished U.S. Appl. No. 17/589,341, filed Jan. 31, 2022 titled "Apple Tree Rootstock Named 'G.66',".

* cited by examiner

*Primary Examiner* — Susan McCormick Ewoldt
(74) *Attorney, Agent, or Firm* — Morrison & Foerster LLP

(57) ABSTRACT

A new and distinct variety of apple tree rootstock *Malus domestica* x *Malus robusta* hybrid 'G.257' is described. The new variety is a semi-dwarfing rootstock that is resistant to fire blight (*Erwinia amylovora*) and crown rot (*Phytophthora cactorum*) and tolerant to the replant disease complex. The 'G.257' rootstock is useful in that it can be propagated clonally and used as a rootstock or root system for apple trees as well as for interstems of apple trees.

8 Drawing Sheets

This invention was made with United States government support under a United States Department of Agriculture—Agricultural Research Station Cooperative Research and Development Agreement, Sponsor's Contract Number 58-3K95-M-1031. The government has certain rights in the invention.

Genus and species: *Malus domestica* x *Malus robusta* hybrid.

Variety denomination: 'G.257'.

BACKGROUND OF THE INVENTION

I. Field & Utility Summary

The invention described herein is a new variety of apple tree rootstock, *Malus domestica* x *Malus robusta* hybrid, hereinafter referred to as 'G.257'. This new apple tree is useful as it can be propagated clonally and used as a root system or interstem for apple trees. This new variety is a semi-dwarfing rootstock that is resistant to fire blight and crown rot and has shown tolerance to the replant disease complex as described in Mazzola, M. 1998. "Elucidation of the microbial complex having a causal role in the development of apple replant disease in Washington." Phytopathology 88:930-938, and having as causative agents *Cylindrocarpon destructans, Phytophthora cactorum, Pythium* spp., and *Rhizoctonia* spp. This new apple rootstock has been shown to induce early bearing on grafted scions, promote larger fruit size, display good productivity and propagate well.

II. Cultivation Summary

'G.257' originated from a planned cross (*Malus domestica* x *Malus robusta* hybrid) in 1976 in Geneva, N.Y.

SUMMARY OF THE INVENTION

The present invention relates to a new and distinct variety of apple tree rootstock named 'G.257.' The 'G.257' apple tree rootstock is a semi-dwarfing rootstock that is resistant to fire blight (*Erwinia amylovora*) and crown rot (*Phytophthora cactorum*). The 'G.257' rootstock is useful in that it can be propagated clonally and used as a rootstock or root system for apple trees as well as for interstems of apple trees. While 'G.257' rootstock is a hybrid from a cross between 'Ottawa 3' (unpatented) and 'Robusta 5' (unpatented), it is distinct from its parent cultivars in terms of dwarfing and disease resistance. The apple tree rootstock 'G.257' produces grafted trees that are 45 to 55 percent of own rooted standard apple trees, displays good uptake of boron, it induces good precocity on the scion and is tolerant to the replant disease complex.

I. Breeding History

In the spring of 1976, pollen from a *Malus robusta* 'Robusta 5' apple tree was applied to emasculated flowers of a *Malus domestica* hybrid 'Ottawa 3' in Geneva, N.Y. In the fall of 1976, seeds resulting from this pollination were extracted from mature fruit derived from this cross. In the winter of 1976-1977, the seeds were stratified and planted in large flats under conditions effective to germinate seeds and obtain seedlings. When germinated seedlings were about 2.5 cm tall they were inoculated with a mixture of isolates of the oomycete (water mold) *Phytophthora cactorum* (the causal agent of crown and root rots). The flats were flooded to mid-hypocotyl level and kept at 23° C. for one week. Surviving seedlings were transplanted into individual pots.

In the summer of 1977, each of the transplanted seedlings was inoculated with approximately $10^6$ colony forming units of the Ea 273 strain of the fire blight bacterium *Erwinia amylovora* by inserting a 26-gauge hypodermic syringe needle into the shoot tip. The seedling designated as #257 was one of the survivors of this battery of inoculations from the same cross. All the surviving plants were transplanted to a research farm (Geneva, N.Y.) in the fall of 1977 and allowed to grow side shoots for propagation/evaluation. From 1981 to 2019, 'G.257' was evaluated for rooting ability (good), lack of spine production in nursery stool bed (produces some spines), and low root brittleness in a layering bed (stool bed). In 1984, at least 4 finished trees with 'G.257' rootstock were planted in a first test orchard on a research farm (Geneva, N.Y.) with *Malus domestica* cv. 'Empire' (unpatented) grafted onto this rootstock as the scion cultivar. This rootstock performed well (top 20% of many rootstocks tested) in these first test trials and during 1990-2018 more material was propagated by stool bed and nursery to be entered into new trials in Geneva, N.Y. with multiple *Malus domestica* scion cultivars including 'Honeycrisp' (U.S. Plant Pat. No. 7,197P), (unpatented), 'Golden Delicious' (unpatented), 'Gala' (unpatented), 'New York 1' (U.S. Plant Pat. No. 22,228P3) and 'Empire'. The 'G.257' rootstock performed well with all the scion cultivars that were tested. Several tests conducted between 2014 and 2020 show that 'G.257' displayed higher than average ability to increase the content of boron in grafted scion leaves.

II. Asexual Reproduction

Asexual reproduction of the 'G.257' apple rootstock has been achieved using the traditional method of clonally propagating apple rootstocks at a research farm in Geneva, N.Y. In particular, the original seedling of the 'G.257' apple rootstock was planted in a research farm (Geneva. N.Y.) and allowed to develop into a "mother plant." The 'G.257' mother plant was then used to obtain rooted liners using conventional layering procedures. The resulting liners were then planted in a row to generate a layering stool bed (also referred to as the "mother stool bed"). The living tissues (i.e. leaves, stems, roots, buds, and spines) of the mother stool bed were observed to be identical to secondary and tertiary stool bed plants. In addition to conventional layering, the 'G.257' apple rootstock variety has been asexually reproduced by root cuttings, by budding and grafting onto seedling and clonal rootstocks, and by in vitro culture in research labs, research farms and greenhouses in Geneva, N.Y.

III. Stability

Observations of trees from these propagations indicate that all trees have proven true to type and identical in all appearances to the original tree.

IV. Comparisons with Parental and Reference Varieties

The seed parent *Malus domestica* hybrid 'Ottawa 3' is a dwarfing rootstock, i.e., trees grown on this rootstock are 25 to 35 percent the size of a standard self-rooted seedling apple tree. 'Ottawa 3' is well known to induce precocity to the scion (i.e., the ability to induce early reproductive development on grafted scions) and has good yield efficiency (i.e., the ability to produce many apples per square cm of trunk). 'Ottawa 3' produces no spines in stool bed clonal propagation, it is winter hardy, but susceptible to the woolly apple aphid (*Eriosoma lanigerum*) and to fire blight (*Erwinia amylavora*) and to the specific replant disease complex.

The pollen parent *Malus robusta* 'Robusta 5' is a non-dwarfing rootstock, i.e. trees on this rootstock grow to the same size of a standard self-rooted apple tree. 'Robusta 5' does not induce precocity to the scion and is not yield efficient. Juvenile plants and young stool propagules of 'Robusta' 5 produce many spines. 'Robusta 5 is resistant to fire blight and powdery mildew (*Podosphaera leoucotricha*), and is immune to the woolly apple aphid. 'Robusta 5' breaks buds very early in the spring and is winter hardy. Further, 'Robusta 5' has shown tolerance to the specific replant disease complex.

The 'G.257' apple rootstock of the present invention has a combination of qualities that distinguishes it from its parental plants (i.e., 'Ottawa 3' and 'Robusta 5'). For example, although 'Ottawa 3 is susceptible to the woolly apple aphid, 'G.257' has resistance to it. The yield efficiency displayed by 'G.257' is less than the 'Ottawa 3' parent because 'G.257' displays semi-dwarfing properties that are intermediate between 'Ottawa 3' and the non-dwarfing parent 'Robusta 5' and thus belongs to an intermediate class? allowing scions grafted on this rootstock to grow 45 to 55 percent of standard own rooted apple tree seedlings. Specifically, G.257 is in the same dwarfing vigor class as industry standard 'Malling 7'. 'G.257' is similar to 'Ottawa 3' because it induces earlier bearing than 'Malling 7' and is more winter hardy than "Malling 7'.

With regard to its 'Robusta 5' parent, 'G.257' is distinguishable in that it is a semi-dwarfing rootstock and is more yield efficient than 'Robusta. 5'. However, like 'Robusta 5', 'G.257' is resistant to fire blight, and the woolly apple aphid (*Eriosoma lanigerum*) and produces some spines (sylleptic small branches) at the base of clonally propagated stool bed shoots. Similar to 'Robusta 5', the root systems of 'G.257' display high level of branching and fine roots. Furthermore, like 'Robusta 5', 'G.257' displays tolerance to the replant disease complex.

As discussed above, 'G.257' is most similar to 'Malling 7' in terms of dwarfing class. However, 'G.257' is resistant to fire blight, is tolerant to the replant disease complex and wooly apple aphid whereas 'Malling 7' is not. 'G.257' shares the same parents as 'G.210' (U.S. Plant Pat. No. 23,337) and 'G.969' (U.S. Plant Pat. No. 24,073) and has similar resistance to fire blight and crown rot and all are categorized as semi-dwarfing. However, 'G.257' possesses unique nutrient uptake, consistently conferring higher boron to grafted scions. 'G.257' may also promote larger fruit in grafted scions like 'Fuji'.

DESCRIPTION OF THE FIGURES

New apple tree rootstock 'G.257' is illustrated by the accompanying photographs. The colors shown are as true as can be reasonably obtained by conventional photographic procedures.

DETAILED BOTANICAL DESCRIPTION OF THE INVENTION

Figure 1:
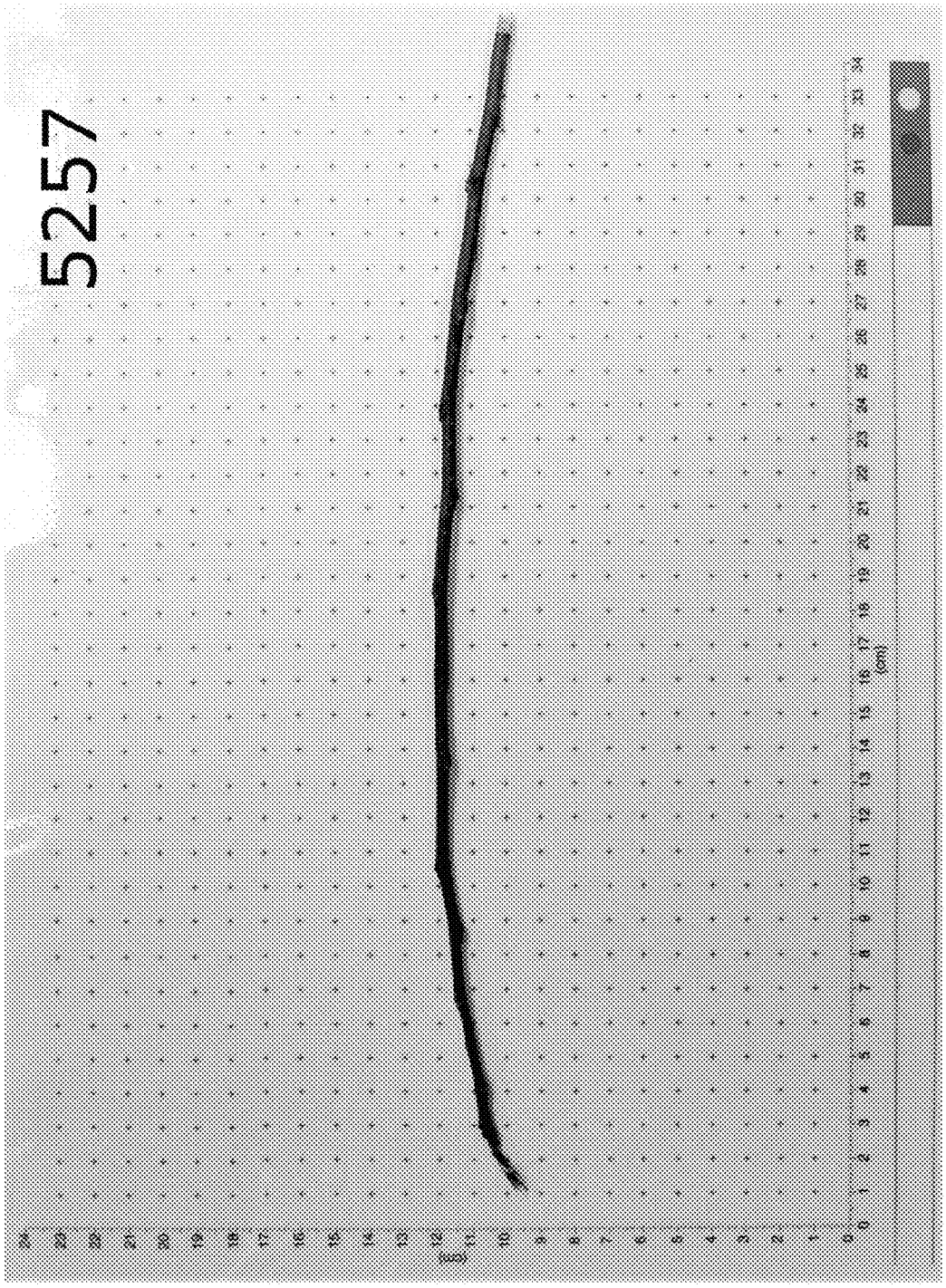
FIG. 1 shows a dormant one-season growth shoot (including buds and bark).
Figure 2:
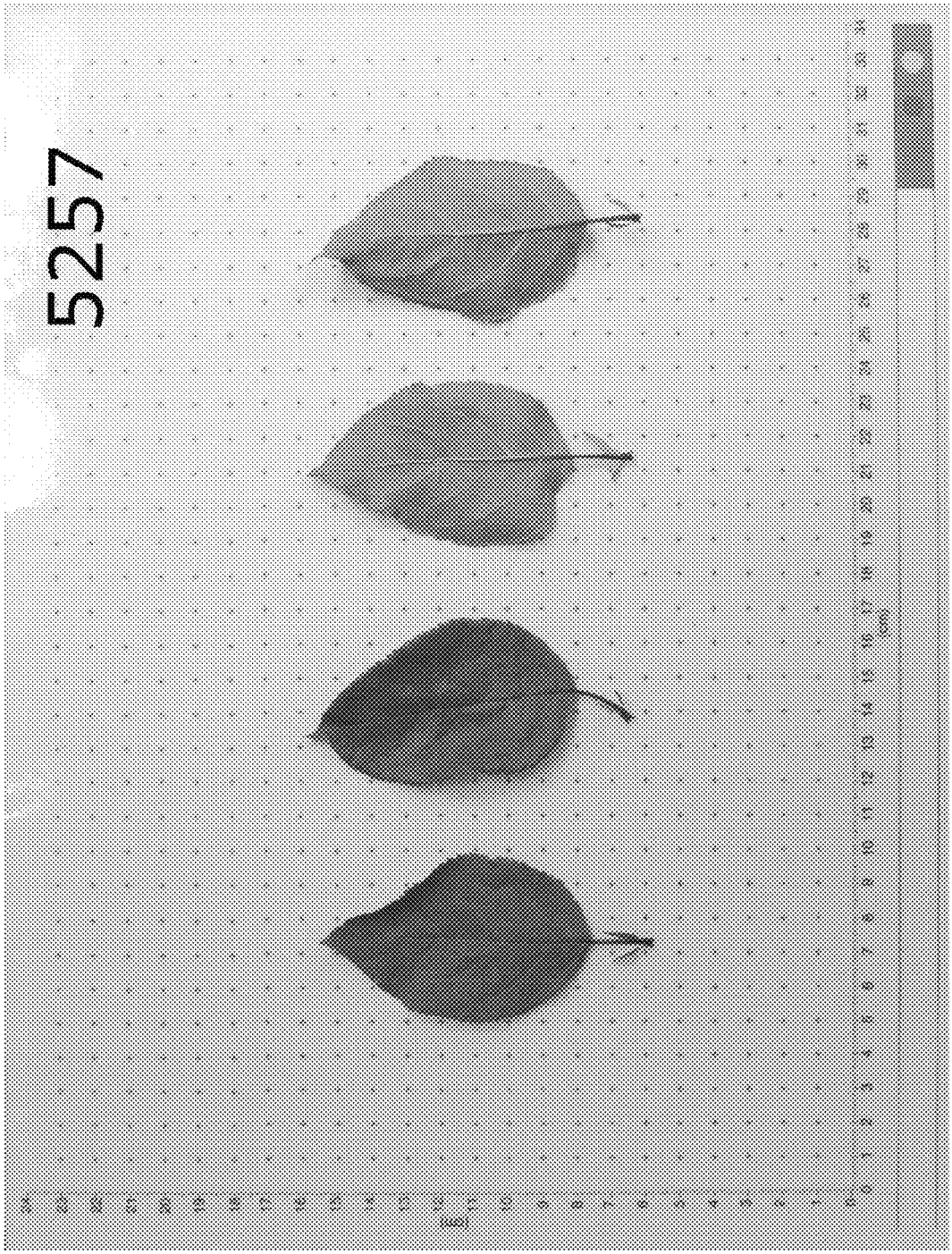
FIG. 2 shows adaxial (upper) and abaxial (lower) laminae of leaves.
Figure 3:
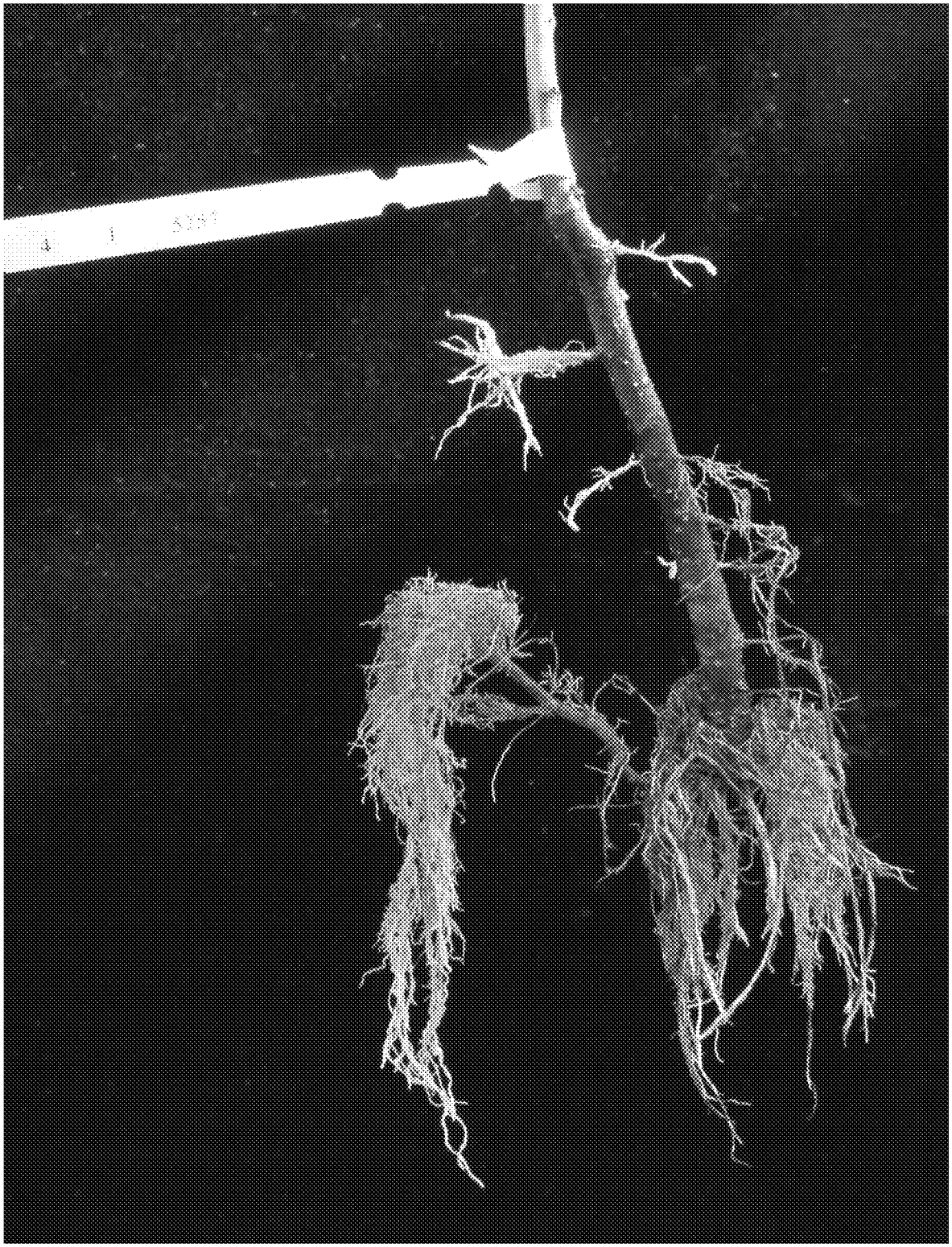
FIG. 3 shows a root system with fine roots.
Figure 4:
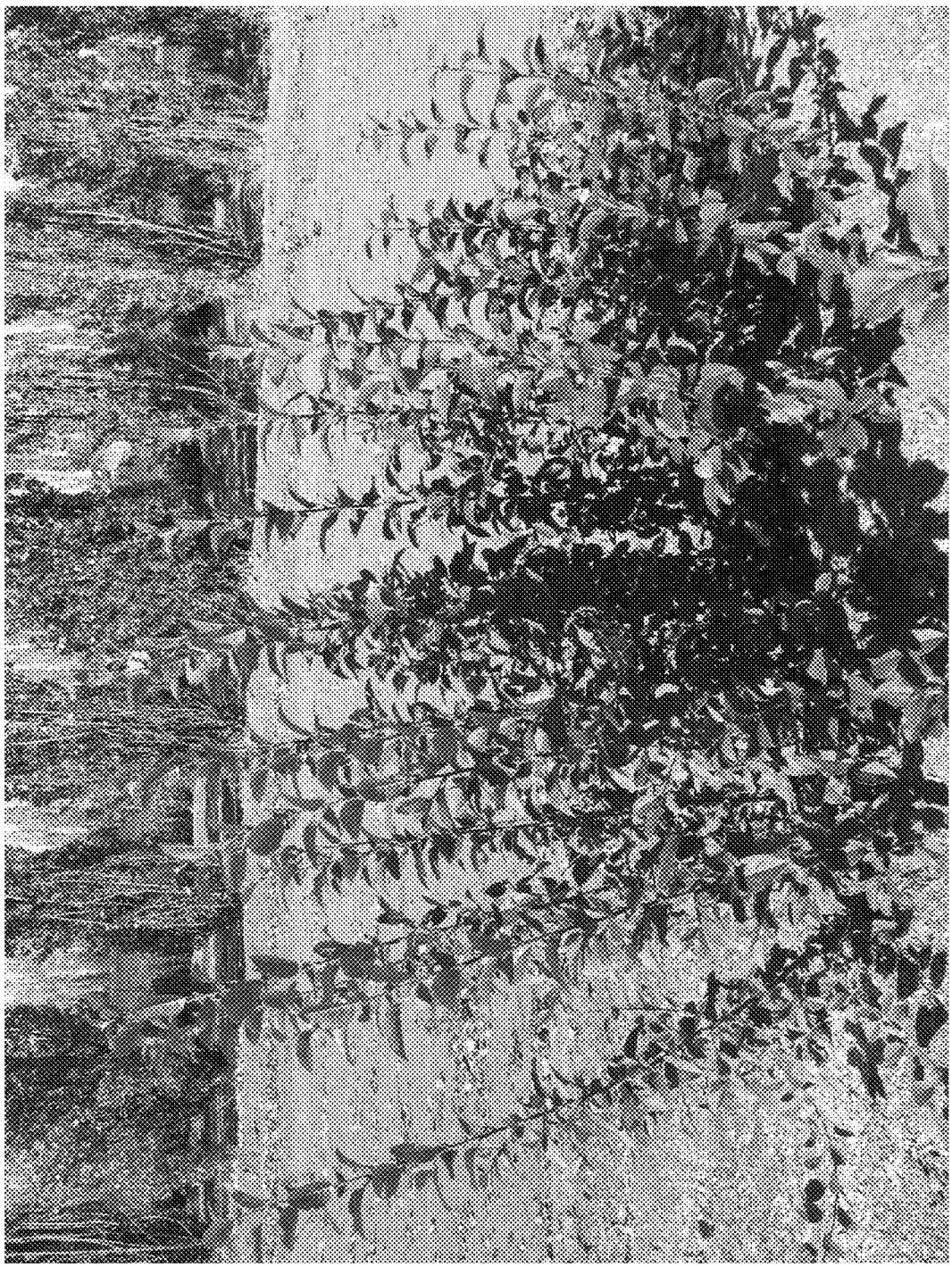
FIG. 4 shows a fully developed stool bed with leaves and shoots.
Figure 5:
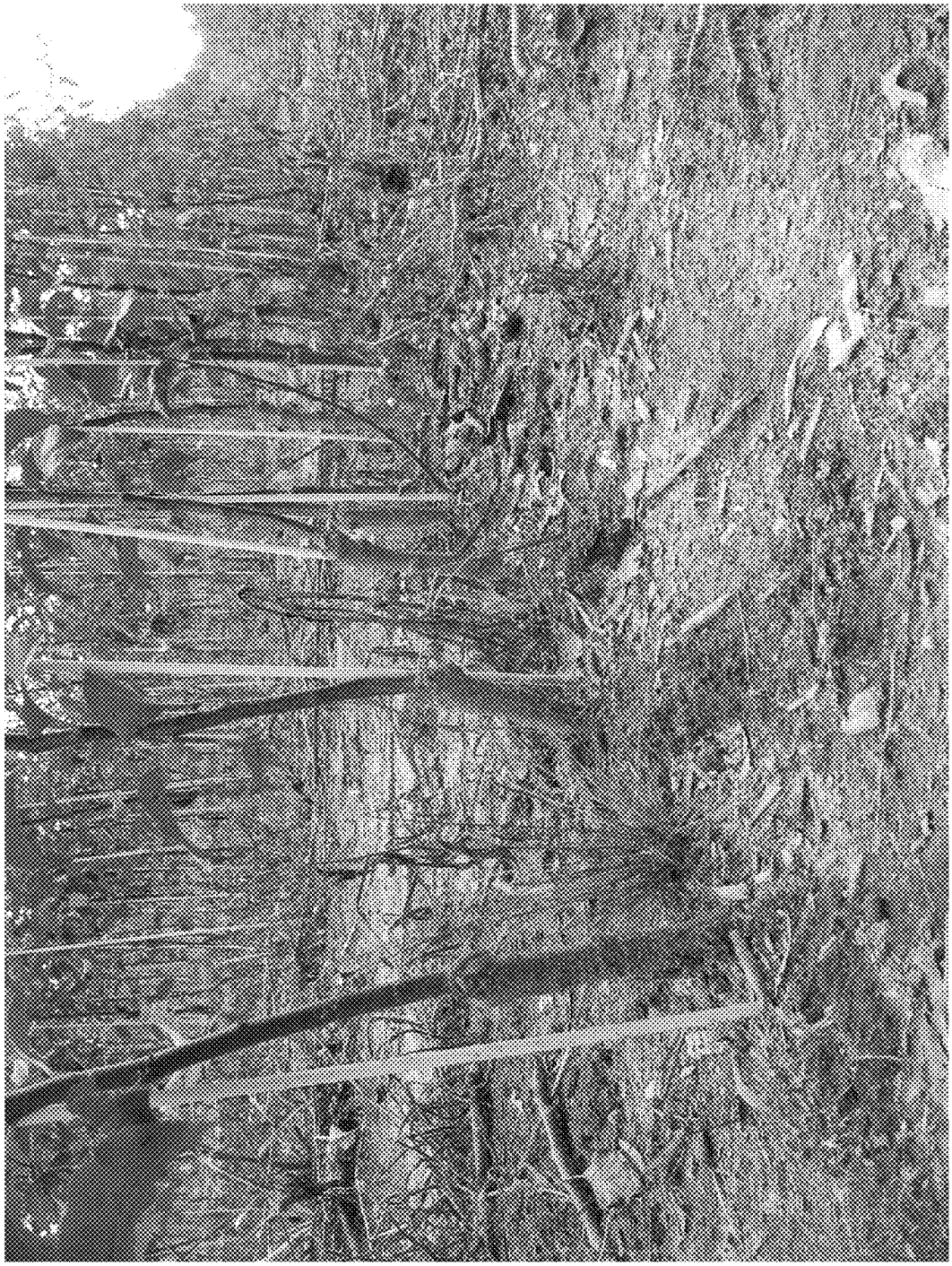
FIG. 5 shows graft unions on finished trees.
Figure 6:
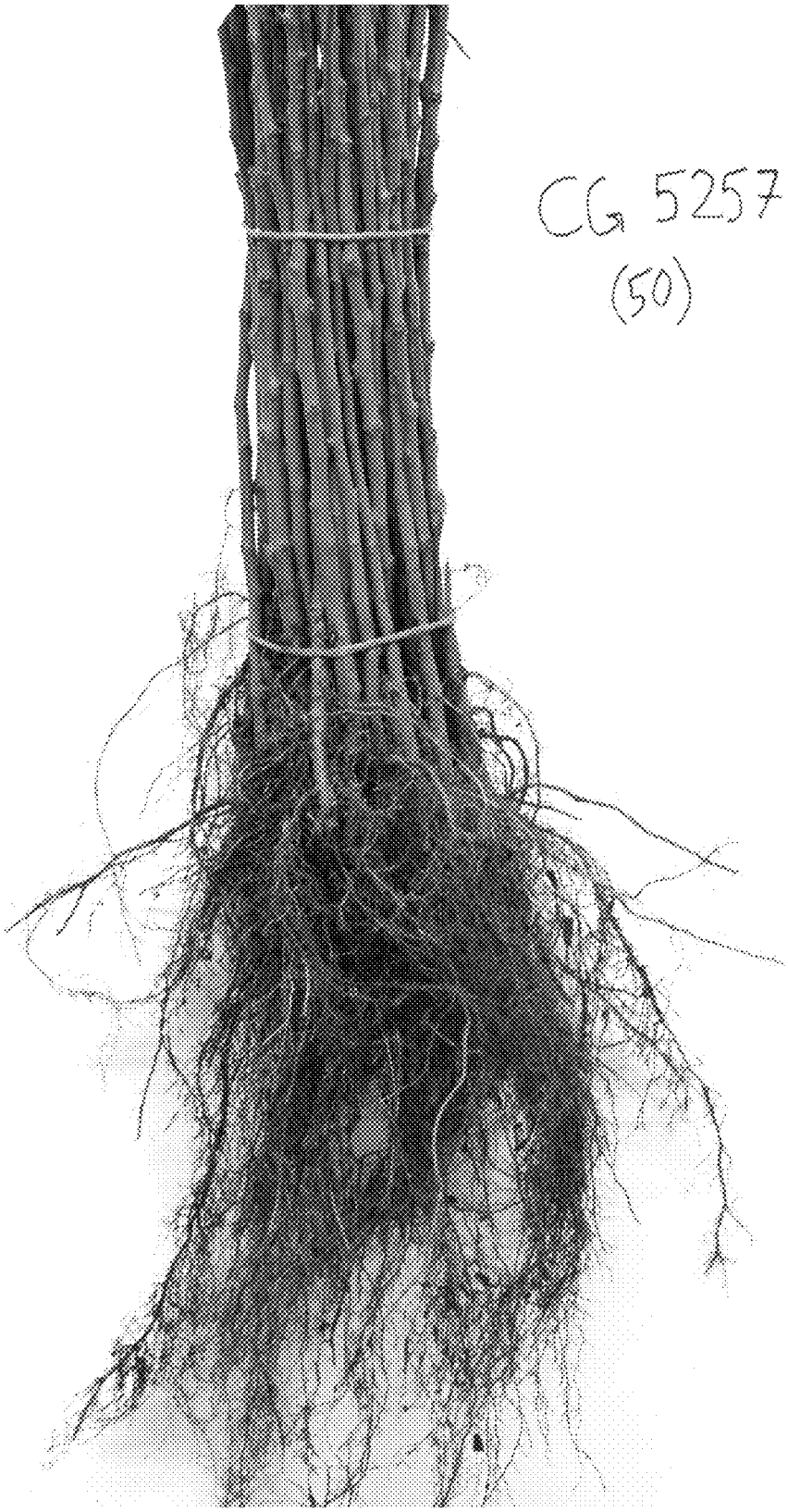
FIG. 6 shows a bundle of rooted rootstock liners.
Figure 7:
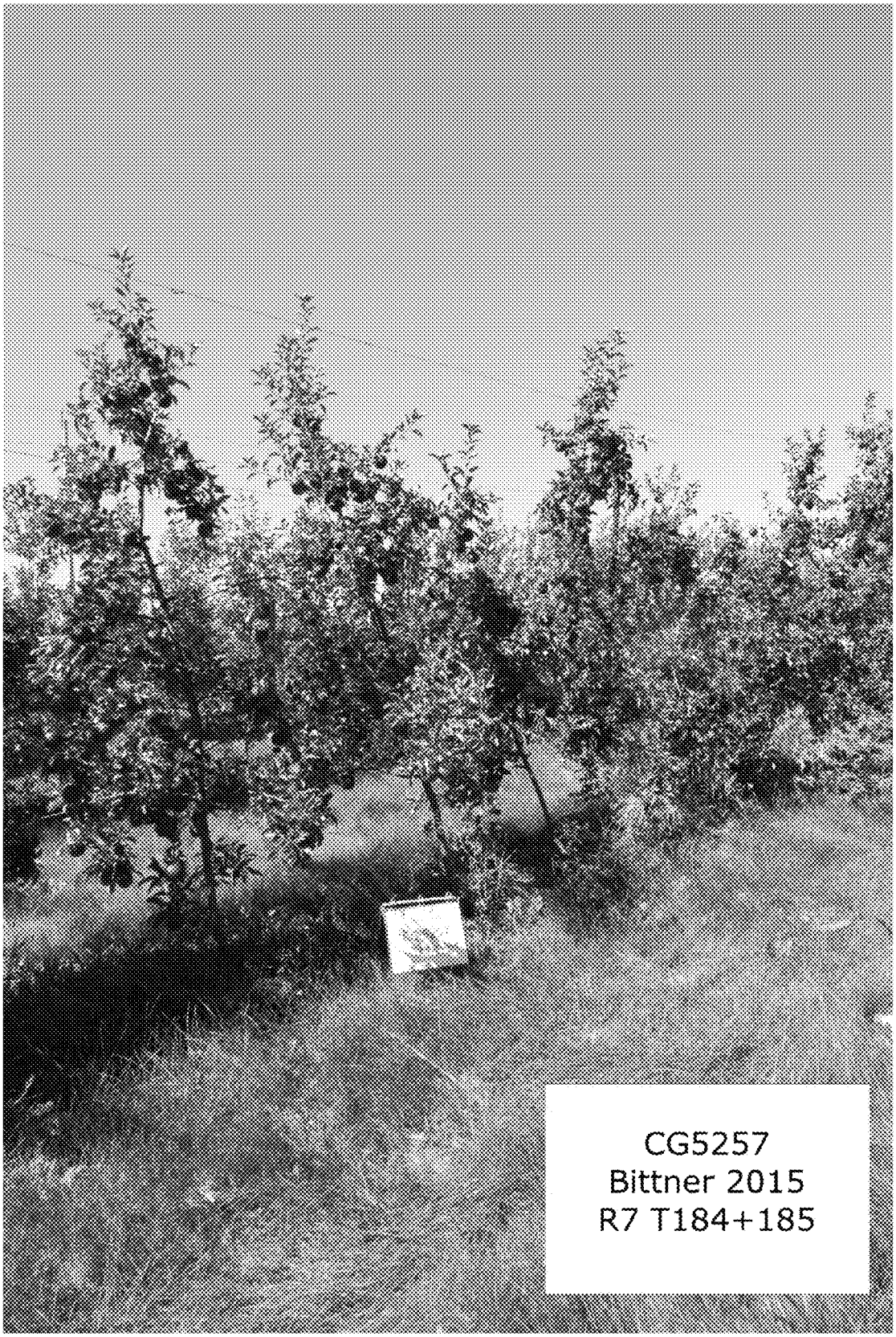
FIG. 7 shows 4-year-old trees in organic production.
Figure 8:
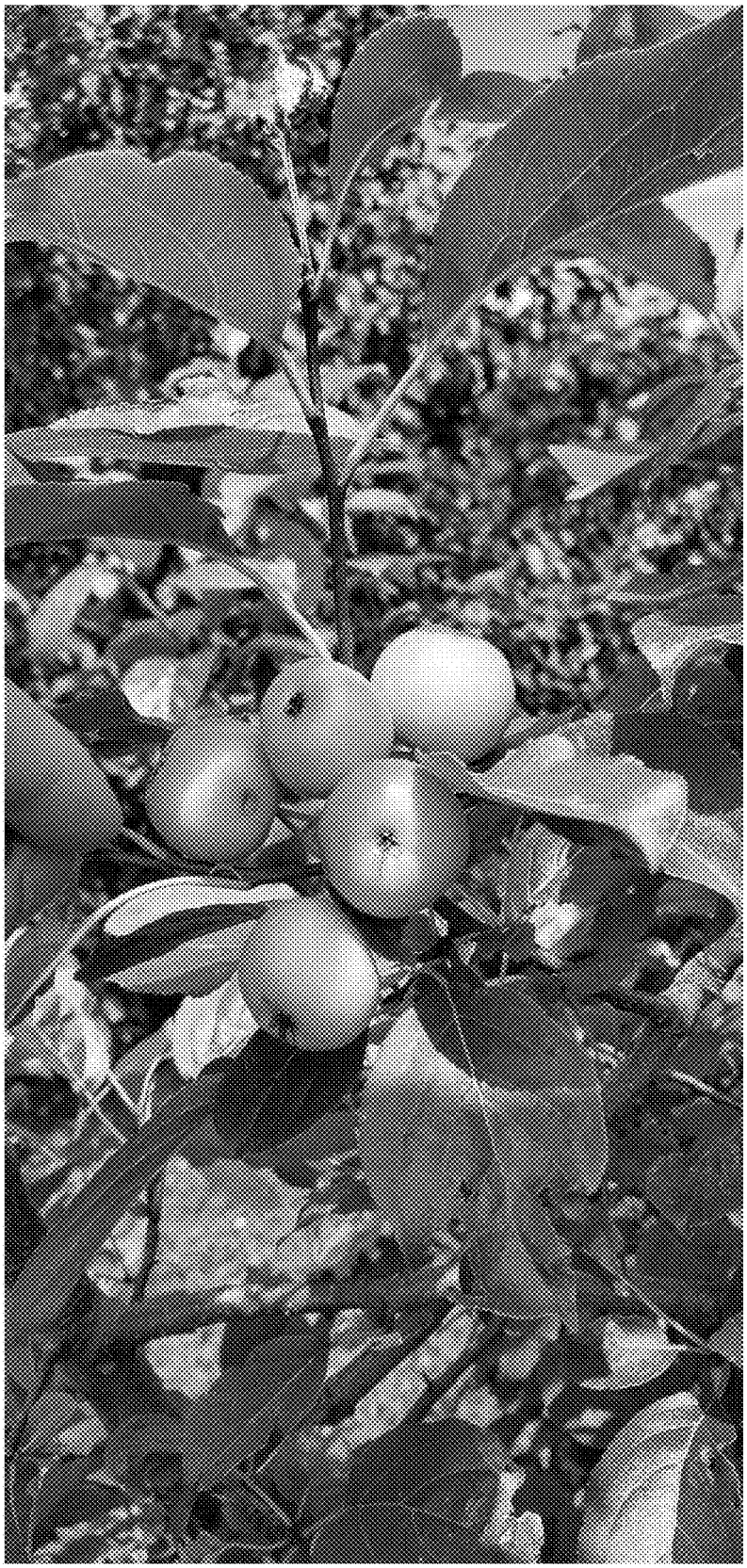
FIG. 8 shows immature fruit.

The following description of apple tree rootstock 'G.257' contains references to color names taken from The Royal Horticultural Society Colour Chart (RHS), 2001 edition. Botanical descriptions follow the Manual of Cultivated Plants (Bailey, 1949).

Tree:

*Habit.*—A self-rooted tree of 'G.257' is a shrub typically standing about 2-2.5 meters tall by about 2 meters wide when 8 years old. A single dominant trunk may develop with highly branched form. When grafted in the orchard it produces very few suckers (i.e., new shoots emerging from below ground). Liners planted in the nursery stop apical growth mid-season.

*Productivity.*—In an intermediate trial performed at a research farm (Geneva, N.Y.), the 'G.257' rootstock received the cultivar 'New York 1' (*Malus domestica*) as the scion and was compared to the *Malus domestica* check rootstocks 'Malling 9' (M.9 EMLA; unpatented), and 'Malling 26' (M.26; unpatented). 'G.257' displayed the highest cumulative yield and was shown to have statistically similar ($p \leq 0.05$) yield efficiency (kg yield/$cm^2$ trunk cross sectional area) as all the check rootstocks.

*Precocity.*—Scion cultivars budded on 'G.257' exhibit the same early bearing/precocity as those budded on 'M.26'.

*Fertility* (*fecundity*).—The 'G.257' plant produces flowers and fruits regularly.

Dormant Shoots (buds and bark):

*Dormant mature shoots.*—Color: Yellow-Green (RHS 146C and 146D) with low exposure to full sunlight grading to Greyed-Orange (RHS 175C and 175D) with full light exposure. Texture: Very light pubescence which gradually disappears in older tissues. Size: 30-60 cm long; can produce sylleptic spines in 10-20% of new shoot depending on sun exposure.

*Axillary buds.*—Size: 3-4 mm long and 3 mm wide with little pubescence. Shape: Obtuse, sessile, somewhat appressed and flattened. Texture: Some pubescence.

*Bark on three-year-old shoots.*—Color: Greyed-Orange (RHS 177C). Lenticels: Color: Greyed-Orange (RHS 164A). Size: 0.3-0.4 mm in diameter. Quantity: 2-3 lenticels per $cm^2$.

Leaves:

*Mature leaves.*—Leaf arrangement: Alternate. Shape: Simple, flat, oblong-ovate. Size: Length: 90 mm. Width: 40 mm at the widest point. Laminae: Somewhat straight. Apex: Acuminate. Base: Nearly symmetrical rounded. Margin: Acutely serrated, with about 6 serrations per cm. Upper surface: Color: Green (RHS 143B). Texture: Glabrous and translucent. Lower surface: Color: Yellow-Green (RHS 144B). Texture: Somewhat pubescent. Venation: Netted. Leaf poise: 15°-25° from the shoot, depending on shoot orientation. Stipules: Length: 9 mm. Width: 2 mm. Petioles: Diameter: 2 mm. Color: Gradation of Greyed-Red (RHS 181A-B) at the base going to Greyed-Red (RHS 179B-C) at the laminae.

Flowers:

*Habit.*—Flowers borne on spurs, shoot terminals, and from lateral buds on growth from previous season.

*Flower diameter.*—40 mm.

*Fragrance.*—None.

*Buds.*—Location: Located on spurs and terminals; are mixed, typically producing a truss of 5 to 6 flowers and one bourse shoot. Shape: Lateral buds are obtuse, sessile and somewhat appressed. Size: Length: 4 mm. Width: 3 mm. Habit: Buds near the base of the shoot of the previous season usually produce 3 to 5 flowers and a single short shoot; mid-shoot buds may have 2-4 flowers; and more distal buds are usually vegetative.

*Petals.*—Size: Length: 25 mm. Width: 18 mm. Shape: Spatulate. Apex: Obtuse. Margin: Smooth. Texture: Smooth. Color: Closed petals: Red (RHS 54A). Open petals: White (RHS 155D) with Red (RHS 54A) striations in some of the petals.

*Reproductive organs.*—Pistils: Length: 6 mm. Color: Yellow-white (RHS 145B). Stamens: Length: 4 mm. Color: White (RHS 155D). Anther color: Yellow-Brown (RHS 167D).

Fruit:

*Mature fruit.*—Size: Height: 30-35 mm. Diameter: 30-35 mm. Shape: Round. Color: Partial Yellow-Orange skin (RHS 21AB) with Red (RHS 43B) blush overtones depending on the exposure to the sun and other growing conditions. Sepals: Persisting on an inset calyx. Flesh: Taste: Astringent (not meant for consumption). Color: Yellow-Orange (RHS 20C). Seed: Color: Greyed-Red (RHS 179A), translucent. Shape: Tear drop shape. Size: Length: 4-6 mm. Diameter: 2-3 mm at the widest point. Number: Generally five seed per fruit.

Disease resistance: As described above, the 'G.257' rootstock of the present invention exhibits resistance to fire blight. The percent lesion measured after inoculation of potted liners in the greenhouse using four different strains of *E. amylovora* was negligible for two of the strains and moderate for the other two, indicating a specific resistance to the bacterium. The 'G.257' rootstock, having survived the inoculation with crown and root rot, is also considered resistant to crown and root rots caused by *Phytophthora cactorum*. 'G.257' displays tolerance to the replant disease complex.

What is claimed is:

1. A new and distinct variety of apple tree rootstock named 'G.257' as herein described and illustrated.

* * * * *